(12) United States Patent
Marrow et al.

(10) Patent No.: US 7,505,127 B2
(45) Date of Patent: *Mar. 17, 2009

(54) ON-LINE RAMAN ANALYSIS AND CONTROL OF A HIGH PRESSURE REACTION SYSTEM

(75) Inventors: David Geoffrey Marrow, Taylor Lake Village, TX (US); David A. Yahn, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 545 days.

This patent is subject to a terminal disclaimer.

(21) Appl. No.: 11/188,276

(22) Filed: Jul. 22, 2005

(65) Prior Publication Data

US 2007/0021586 A1    Jan. 25, 2007

(51) Int. Cl.
*G01J 3/44* (2006.01)
(52) U.S. Cl. .................................................... 356/301
(58) Field of Classification Search .................. 356/301
See application file for complete search history.

(56) References Cited

U.S. PATENT DOCUMENTS

| | | |
|---|---|---|
| 3,725,378 A | 4/1973 | Chamberlin |
| 3,779,712 A | 12/1973 | Calvert et al. |
| 4,175,169 A | 11/1979 | Beals et al. |
| 4,182,810 A | 1/1980 | Willcox |
| 4,243,619 A | 1/1981 | Fraser et al. |
| 4,469,853 A | 9/1984 | Mori |
| 4,540,753 A | 9/1985 | Cozewith et al. |
| 4,543,399 A | 9/1985 | Jenkins, III et al. |
| 4,588,790 A | 5/1986 | Jenkins, III et al. |
| 4,620,049 A | 10/1986 | Schmidt et al. |
| 4,621,952 A | 11/1986 | Aronson |
| 4,888,704 A | 12/1989 | Topliss et al. |
| 5,096,634 A | 3/1992 | Tsadares et al. |
| 5,121,337 A | 6/1992 | Brown |
| 5,151,474 A | 9/1992 | Lange et al. |

(Continued)

FOREIGN PATENT DOCUMENTS

EP     238 796 A2    9/1987

(Continued)

OTHER PUBLICATIONS

J.M. Tedesco et al., "Calibration of dispersive Raman process analyzers," Part of the SPIE Conference on Online Chemical Process Monitoring w/Advanced Techniques, SPIE, vol. 3537, pp. 200-212, Nov. 1998.

(Continued)

*Primary Examiner*—Kara E Geisel
(74) *Attorney, Agent, or Firm*—Amy C. Trexler; Kevin M. Faulkner

(57) ABSTRACT

Methods and systems for analysis of the polymerization material of high pressure polymerization processes are provided. In certain embodiments, the methods and systems subject the polymerization material to Raman spectroscopy analysis. The Raman spectroscopy provides analysis of reaction mixtures and/or product streams in high pressure polymerization processes. The Raman spectroscopy analysis may include both compositional and characterization analysis of the reaction mixtures and product streams. The spectroscopy results can be used to provide process control feedback to adjust operating parameters of the reactor operations and/or an associated polymerization product handling and finishing processes.

29 Claims, 3 Drawing Sheets

U.S. PATENT DOCUMENTS

| | | | |
|---|---|---|---|
| 5,202,395 | A | 4/1993 | Chambon |
| 5,270,274 | A | 12/1993 | Hashiguchi et al. |
| 5,274,056 | A | 12/1993 | McDaniel et al. |
| 5,352,749 | A | 10/1994 | DeChellis et al. |
| 5,405,922 | A | 4/1995 | DeChellis et al. |
| 5,436,304 | A | 7/1995 | Griffin et al. |
| 5,462,999 | A | 10/1995 | Griffin et al. |
| 5,589,555 | A | 12/1996 | Zboril et al. |
| 5,638,172 | A | 6/1997 | Alsmeyer et al. |
| 5,675,253 | A | 10/1997 | Smith et al. |
| 5,678,751 | A | 10/1997 | Buchanan et al. |
| 5,682,309 | A | 10/1997 | Bartusiak et al. |
| 5,684,580 | A * | 11/1997 | Cooper et al. ............... 356/301 |
| 5,696,213 | A | 12/1997 | Schiffino et al. |
| 5,864,403 | A | 1/1999 | Ajji et al. |
| 5,892,228 | A | 4/1999 | Cooper et al. |
| 5,999,255 | A | 12/1999 | Dupée et al. |
| 6,072,576 | A | 6/2000 | McDonald et al. |
| 6,144,897 | A | 11/2000 | Selliers |
| 6,204,344 | B1 | 3/2001 | Kendrick et al. |
| 6,204,664 | B1 | 3/2001 | Sardashti et al. |
| 6,218,484 | B1 | 4/2001 | Brown et al. |
| 6,228,793 | B1 | 5/2001 | Hosaka et al. |
| 6,239,235 | B1 | 5/2001 | Hottovy et al. |
| 6,281,300 | B1 | 8/2001 | Kendrick |
| 6,380,325 | B1 | 4/2002 | Kendrick |
| 6,405,579 | B1 | 6/2002 | Tjahjadi et al. |
| 6,479,597 | B1 | 11/2002 | Long et al. |
| 6,608,678 | B1 * | 8/2003 | Potyrailo et al. ............ 356/301 |
| 6,673,878 | B2 | 1/2004 | Donck |
| 2002/0156205 | A1 | 10/2002 | Long et al. |
| 2004/0133364 | A1* | 7/2004 | Marrow et al. ................ 702/30 |
| 2004/0198927 | A1 | 10/2004 | Battiste |
| 2004/0233425 | A1 | 11/2004 | Long et al. |
| 2004/0266959 | A1 | 12/2004 | Heslop et al. |
| 2005/0154155 | A1* | 7/2005 | Battiste ...................... 356/301 |
| 2007/0019191 | A1* | 1/2007 | Marrow et al. .............. 356/301 |

FOREIGN PATENT DOCUMENTS

| | | |
|---|---|---|
| EP | 257 316 A1 | 3/1988 |
| EP | 257 316 B1 | 3/1988 |
| EP | 328 826 | 8/1989 |
| EP | 561 078 | 9/1993 |
| EP | 406 805 B1 | 12/1995 |
| EP | 561 78 B1 | 4/1997 |
| JP | 02038841 | 2/1990 |
| WO | WO 94/21962 | 9/1994 |
| WO | WO 96/41822 | 12/1996 |
| WO | WO 98/08066 | 2/1998 |
| WO | WO 99/01750 | 1/1999 |
| WO | WO 01/09201 | 2/2001 |
| WO | WO 01/09203 | 2/2001 |
| WO | WO 03/042646 * | 5/2003 |
| WO | WO 2004/063234 | 7/2004 |
| WO | WO 2005/049663 | 6/2005 |

OTHER PUBLICATIONS

A.C. Ouano et al., "Gel Permeation Chromatography," Polymer Molecular Weights Part II, Chapter 6, pp. 287-378, 1975.

Verstrate et al., "Near Monodisperse Ethylene-Propylene Copolymers by Direct Ziegler-Natta Polymerization. Preparation, Characterization, Properties," Macromolecules, vol. 21, pp. 3360-3371, 1988.

F. Rodriguez, "Principles of Polymer Systems 3rd Ed.," Hemisphere Pub. Corp., NY, pp. 155-160, 1989.

Erlich, P., et al., "Fundamentals of the Free-Radical Polymerization of Ethylene," Advances in Polymer Science, vol. 7, pp. 386-448, 1970.

K.R. Beebe et al., "An Introduction to Multivariate Calibration and Analysis," Analytical Chemistry, vol. 59, No. 17, pp. 1007A-1017A, Sep. 1, 1987.

J. M. Tedesco et al., "Calibration of dispersive Raman Process Analyzers," The Society Of Photo-Optical Instrumentation Engineers, vol. 3537, pp. 200-212, 1999.

G.A. Bakken et al., "Examination of Criteria for Local Model Principal Component Regression," Society for Applied Spectroscopy, vol. 51, No. 12, pp. 1814-1822, 1997.

M.L. Myrick et al., "In Situ Fiber-Optic Raman Spectroscopy of Organic Chemistry in a Supercritical Water Reactor," Journal of Raman Spectroscopy, vol. 25, pp. 59-65, 1994.

T. Naes et al., "Locally Weighted Regression and Scatter Correction for Near-Infrared Reflectance Data," Analytical Chemistry, vol. 62, pp. 664-673, 1990.

G.G. Ardell et al., "Model Prediction for Reactor Control," Chemical Engineering Progress, American Institute of Chemical Engineers, vol. 79, No. 6, pp. 77-83, Jun. 1, 1983.

J.J. Zacca et al., "Modelling of the Liquid Phase Polymerization of Olefins in Loop reactors," Chemical Engineering Science, vol. 48, No. 22, pp. 3743-3765, 1993.

L.P. Russo et al., "Moving-Horizon State Estimation Applied to an Industrial Polymereization Process," American Control Conf. Proc., San Diego, CA, 1999.

H. Martens et al., "Multivariate Calibration," Wiley & Sons Ltd., pp. viii-ix, 1989.

Multivariate Data Analysis for Windows—Version 3.0, excerpted from Pirouette Software Manual, Exploratory Analysis: Principal Component Analysis, pp. 5-13 through 5-40, 1985-2000.

E.P.C. Lai et al., "Noninvasive Spectroscopic Detection of Bulk Polymerization by Stimulated Raman Scattering," Applied Spectroscopy, vol. 48, No. 8, 1994.

S. Sekulic et al., "Nonlinear Multivariate Calibration Methods in Analytical Chemistry," Analytical Chemistry, vol. 65, No. 19, pp. 835A-845A, Oct. 1, 1993.

E.D. Lipp et al., "On-Line Monitoring Of Chlorosilane Streams By Raman Spectroscopy," Reprinted from Applied Spectroscopy, vol. 52, No. 1, Jan. 1998.

D.R. Battiste et al., "On-Line Raman Analysis of Ethylene and Hexene in the Phillips 1-Hexene and Polyethylene Processes," Gulf Coast Conference presentation (Abstract) Sep. 2000.

M.J. Pelletier et al.; "Optical fibers enable Raman instruments to analyze industrial process problems quickly and accurately," Raman Spectroscopy—Keeps Industry Under Control, Reprint: Photonics Spectra, 4 pgs., Oct. 1997.

V. Centner et al., "Optimization in Locally Weighted Regression," Analytical Chemistry, vol. 70, No. 19, pp. 4206-4211, Oct. 1, 1998.

"Principal Components Analysis," excerpted from PLS_Toolbox, Version 2.0 Data Analysis Manual, Eigenvector Research, Inc., pp. 32-34, 1998.

L. Markwort et al., "Raman Imaging of Heterogeneous Polymers: A Comparison of Global versus Point Illumination," Applied Spectroscopy, vol. 49, No. 10, pp. 1411-1430, 1995.

I. Modric et al., "Raman- und Infrarotspektren isotaktischer Polyalkylathylene*," Colloid & Polymer Sci., vol. 254, pp. 342-347, 1976.

M.G. Hansen et al., "Real-Time Monitoring of Industrial Polymers," Raman Review; pp. 1-4, Mar. 1998.

S.E. Nave "Rugged Fiber Optic Probes and Sampling Systems for Remote Chemical Analysis Via the Raman Technique," ISA, Paper #96-042, pp. 453-467, 1996.

M.J. Pelletier et al., "Shining a Light on Wet Process Control," Semiconductor International, 4 pages, Mar. 1996.

K.P.J. Williams et al., "Use of Micro Raman Spectroscopy for the Quantitative Determination of Polyethylene Density Using Partial Least-Squares Calibration," Journal of Raman Spectroscopy, vol. 26, pp. 427-433, 1995.

* cited by examiner

US 7,505,127 B2

ON-LINE RAMAN ANALYSIS AND CONTROL OF A HIGH PRESSURE REACTION SYSTEM

FIELD OF THE INVENTION

This disclosure relates to methods and systems for measuring polymeric properties and controlling polymer production, finishing, and processing processes of high pressure reaction systems using the measured properties.

BACKGROUND OF THE INVENTION

It is known that monomers, such as ethylene, propylene, and other olefins, may be polymerized at high pressures in combination with high temperatures. Typically the polymerization reaction occurs within a reactor where the pressure ranges from about 20 MPa to in excess of 300 MPa. In situations when the pressure equals or exceeds 110 MPa, the polymerization reaction is considered a high pressure reaction thereby requiring a high pressure reactor. Exemplary high pressure reaction systems are disclosed in the following references: U.S. Pat. No. 3,725,378 to Chamberlin, U.S. Pat. No. 4,175,169 to Beals et al., and U.S. Pat. No. 6,673,878 to Donck.

Conventional systems for controlling high pressure polymerization processes include sampling and analyzing a product stream downstream of the reactor. These control systems are time intensive and analytical results are usually available only every 2 to 4 hours. In commercial scale polymerization processes, many thousands of tons of product can be produced in the time span of 2 to 4 hours. Accordingly, conventional control systems may result in the production of a large amount of off-spec product.

SUMMARY OF THE INVENTION

This disclosure relates to methods and systems for analysis of reaction mixtures and product streams of high pressure reaction systems. The results of the analysis may in turn be used to control the high pressure polymerization process and/or finishing and handling processes for the polymerization product produced in the high pressure processes.

In certain embodiments, the methods and systems described herein analyze reaction mixtures and/or product streams in high pressure polymerization processes by Raman spectroscopy analysis. The Raman spectroscopy analysis may include both compositional and characterization analysis of the reaction mixtures and product streams. The spectroscopy results can be used to provide process control feedback to adjust operating parameters of the reactor operations and/or an associated polymerization product handling and finishing processes.

DETAILED DESCRIPTION OF THE INVENTION

Figure 1:
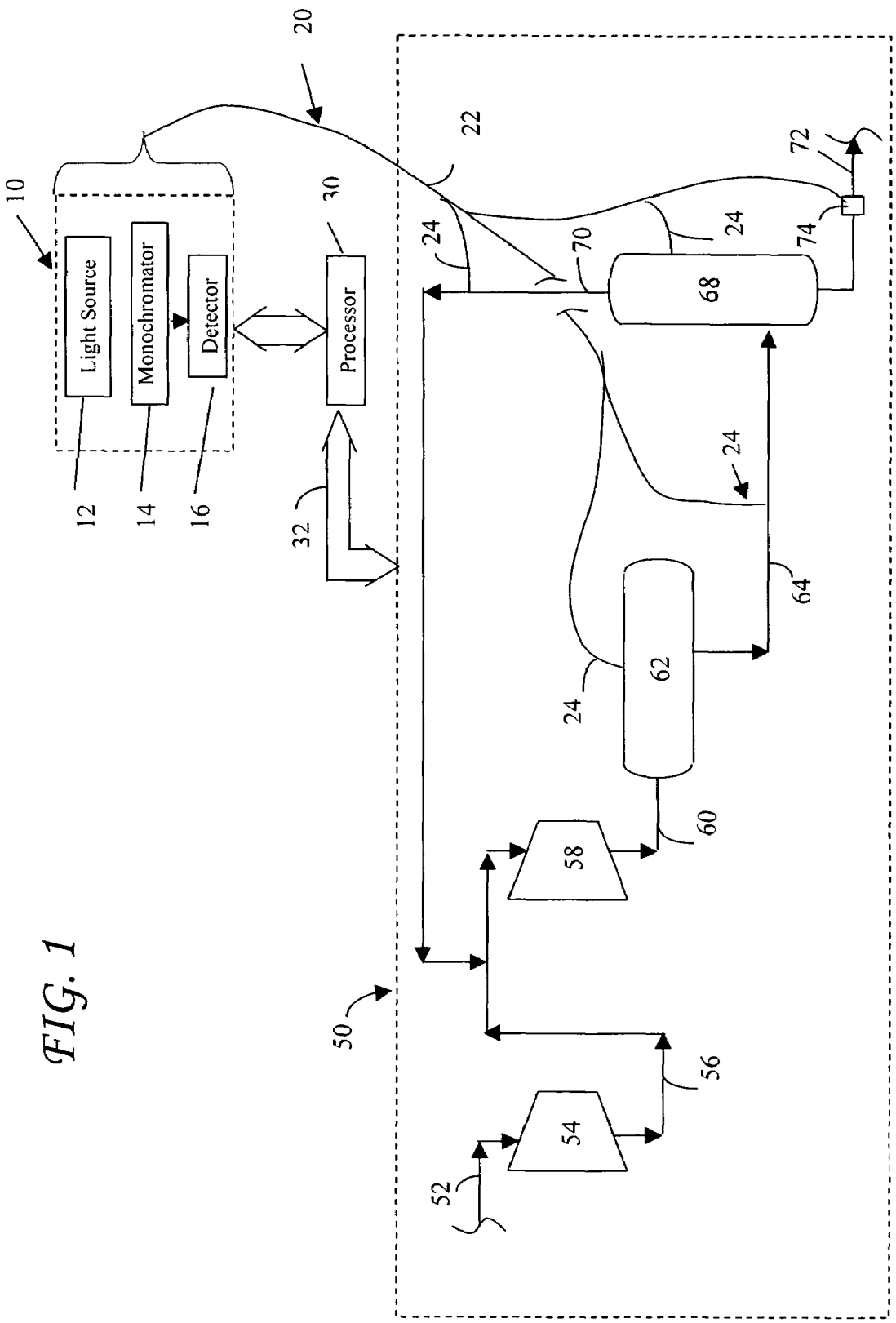
FIG. 1 is a block diagram of a Raman analyzer system coupled with a high pressure reactor system.

This disclosure relates to the use of spectroscopic techniques to determine various properties of reaction mixtures within the reaction zone of a high pressure reaction system, that includes a high pressure polymerization reactor and polymer product streams downstream of the reaction zone of a high pressure polymerization reactor. For purposes of this disclosure, the term "high pressure polymerization reactor" refers to polymerization reactors in which the reaction zone is maintained at a temperature of about 120° C. to about 355° C. and a pressure of about 110 MPa to about 350 MPa during the polymerization process. Tubular high pressure reactors typically operate at a temperature of about 120° C. to about 355° C. and a pressure of about 210 MPa to about 310 MPa. Autoclave high pressure reactors typically operate at a temperature of about 210° C. to about 310° C. and a pressure of about 110 MPa to about 220 MPa.

This disclosure also relates to using the determined properties to control the high pressure polymerization process. The values determined may include compositional values and a variety of characterization values. The various properties that may be analyzed will be discussed in more detail hereinafter.

In one embodiment, Raman spectroscopy is employed for use in this disclosure. In certain embodiments, the methods and systems described herein include the placement of at least one Raman probe into a high pressure polymerization process system.

Raman spectroscopy is a known analytical tool for molecular characterization, identification, and quantification. Raman spectroscopy makes use of inelastically scattered radiation from a non-resonant, non-ionizing radiation source, typically a visible source such as a laser, to obtain information about molecular vibrational-rotational states. In general, non-ionizing, non-resonant radiation is scattered elastically and isotropically (Raleigh scattering) from a scattering center, such as a molecule. Subject to well-known symmetry and selection rules, a very small fraction of the incident radiation can be inelastically and isotropically scattered, with each inelastically scattered photon having an energy $E=h\nu_0 \pm |E_{i',j'}-E_{i,j}|$, where $h\nu_0$ is the energy of the incident photon and $|E_{i',j'}-E_{i,j}|$ is the absolute difference in energy between the final (i',j') and initial (i,j) vibrational-rotational states of the molecule. This inelastically scattered radiation is the Raman scattering, and includes both Stokes scattering, where the scattered photon has lower energy than the incident photon ($E=h\nu_0-|E_{i',j'}-E_{i,j}|$), and anti-Stokes scattering, where the scattered photon has higher energy than the incident photon ($E=h\nu_0+|E_{i',j'}-E_{i,j}|$).

Raman spectra are typically shown as plots of intensity (arbitrary units) versus "Raman shift," where the Raman shift is the difference in energy or wavelength between the excitation radiation and the scattered radiation. The Raman shift is typically reported in units of wavenumbers (cm$^{-1}$), i.e., the reciprocal of the wavelength shift in centimeters. The energy difference $|E_{i',j'}-E_{i,j}|$ and wavenumbers ($\omega$) are related by the expression $|E_{i',j'}-E_{i,j}|=hc\omega$, where h is Planck's constant, c is the speed of light in cm/s, and $\omega$ is the reciprocal of the wavelength shift in centimeters.

The spectral range of the Raman spectrum acquired is broad. However, in one embodiment, a useful range includes Raman shifts (Stokes and/or anti-Stokes) corresponding to a typical range of polyatomic vibrational frequencies, generally from about 0 cm$^{-1}$ to about 4000 cm$^{-1}$. It should be appreciated that useful spectral information is present in lower and higher frequency regions. For example, numerous low frequency molecular modes contribute to Raman scattering in the region below 100 cm$^{-1}$ Raman shift, and overtone vibrations (harmonics) contribute to Raman scattering in the region above 4000 cm$^{-1}$ Raman shift. Thus, if desired, acquisition and use of a Raman spectrum as described herein can include these lower and higher frequency spectral regions.

Conversely, the spectral region acquired can be less than all of the 100 cm$^{-1}$ to 4000 cm$^{-1}$ region. For many polymers the majority of Raman scattering intensity will be present in a region from about 500 cm$^{-1}$ to about 3500 cm$^{-1}$ or from 1000 cm$^{-1}$ to 3000 cm$^{-1}$. The region acquired can also include a variety of sub-regions that need not be contiguous. In certain embodiments, range of polyatomic vibrational frequencies acquired is about 0 cm$^{-1}$ to about 1900 cm$^{-1}$. In certain embodiments, range of polyatomic vibrational frequencies acquired is about 400 cm$^{-1}$ to about 1800 cm$^{-1}$.

As explained below, it is a particular advantage of the methods and systems described herein that Raman scattering intensity data is useful in determining properties of polymer particles without the need to identify, select, or resolve particular spectral features. Thus, it is not necessary to identify a particular spectral feature as being due to a particular mode of a particular moiety of the polymer, nor is it necessary to selectively monitor Raman scattering corresponding to a selected spectral feature. Indeed, it has been surprisingly found that such selective monitoring disadvantageously disregards a wealth of information content embedded in the spectrum that, heretofore, has generally been considered to be merely unusable scattering intensity disposed between and underlying the identifiable (and thus presumed useful) bands. Accordingly, in the methods described herein, the Raman spectral data acquired and used includes a plurality of frequency or wavelength shift, scattering intensity (x, y) measurements over relatively broad spectral regions, including regions conventionally identified as spectral bands and regions conventionally identified as interband, or unresolved regions.

The frequency spacing of acquired data can be readily determined by one skilled in the art, based on considerations of machine resolution and capacity, acquisition time, data analysis time, and information density. Similarly, the amount of signal averaging used is readily determined by one skilled in the art based on machine and process efficiencies and limitations.

In certain embodiments, the data is acquired in a continuous manner by repeating the data acquisition and analysis at designated time intervals. In specific embodiments, the data acquisition and analysis is repeated at time intervals of about 1 to about 5 minutes.

The spectral region measured can include Stokes scattering (i.e., radiation scattered at frequencies lower than the excitation frequency), anti-Stokes scattering (i.e., radiation scattered at frequencies higher than the excitation frequency), or both. Optionally, polarization information embedded in the Raman scattering signal can also be used, and one skilled in the art readily understands how to acquire Raman polarization information. However, determining polymer properties as described herein does not require the use of polarization information.

FIG. 1 provides a schematic representation of an embodiment of the methods and systems described herein. A Raman spectral system is implemented to monitor characteristics of a reaction mixture of the depicted high pressure polymerization process and/or the various polymer product streams produced in the high pressure polymerization process, including streams exiting the reactor and product streams further downstream from the reactor. For the purposes of this disclosure, the reaction mixture and/or the polymer product streams shall collectively be referred to as "polymerization material." In other words, polymerization material refers to the mixture of monomer, solvent, initiator/catalyst, and alternatively modifier, and polymer product forming the reaction mixture within the reactor 62. Polymerization material also refers to the unfinished and finished polymer product streams progressing through various finishing and handling processes downstream of the reactor 62, including any unreacted monomer, solvent or other materials in the polymer product streams.

Generally, in the high pressure processes described herein, the pressure within the system drops progressively at locations within the system further from the reactor. In certain embodiments, the term "polymerization material" refers to material in the system at pressures of about 0.5 MPa or higher. In exemplary systems, pressures of about 0.5 MPa are present at the exit of the low pressure separator. In other embodiments, the term "polymerization material" refers to material in the system at pressures of about 1.5 MPa or higher. In exemplary systems, pressures of about 1.5 MPa are present at the exit of the low pressure separator. In additional embodiments, the term "polymerization material" refers to material in the system at pressures of about 5 MPa or higher. In exemplary systems, pressures of about 5 MPa are present at the exit of the low pressure separator.

The instrumentation used to collect and process Raman data includes a Raman spectrometer system 10, a transmittance system 20, a control loop 32, and a processor 30. The Raman spectrometer system 10 comprises a Raman spectrometer, the principal components of which are light source 12, a monochromator 14, and a detector 16. Raman spectrometers are well-known analytical instruments, and thus only a brief description is provided herein. Additional detail is provided in published patent application US 2004/0233425, having the same assignee as the present application.

The Raman spectrometer system 10 includes a light source 12 that delivers excitation radiation to at least one probe 24. Scattered radiation is collected, filtered of Raleigh scattered light, and dispersed via a monochromator 14. The dispersed Raman scattered light is then imaged onto a detector 16 and subsequently processed within the processor 30, as described in more detail hereinafter.

The excitation source and frequency can be readily determined based on considerations well-known in the art. Typically, the light source 12 is a visible laser, such as a frequency-doubled Nd:YAG laser (532 nm), a helium-neon laser (633 nm), or a solid-state diode laser (such as 785 nm). The laser can be pulsed or continuous wave (CW), polarized as desired or randomly polarized, and preferably single-mode. Typical excitation lasers will have 100 to 400 mW power (CW), although lower or higher power can be used as desired. Light sources other than lasers can be used, and wavelengths and laser types and parameters other than those listed above can also be used. It is well-known that scattering, including Raman scattering, is proportional to the fourth power of the excitation frequency, subject to the practical limitation that fluorescence typically overwhelms the relatively weak Raman signal at higher frequencies. Thus, higher frequency (shorter wavelength) sources are preferred to maximize signal, while lower frequency (longer wavelength) sources are preferred to minimize fluorescence. One skilled in the art can readily determine the appropriate excitation source based on these and other considerations, such as mode stability, maintenance time and costs, capital costs, and other factors well understood in the art.

The excitation radiation can be delivered to the at least one probe 24, and the scattered radiation collected from the at least one probe 24, by any convenient means known in the art, such as conventional beam manipulation optics or fiber optic cables generally designated 20. For an on-line process measurement, it is particularly convenient to deliver the excitation radiation and collect the scattered radiation through fiber optic cables. It is a particular advantage of Raman spectroscopy that the excitation radiation typically used is readily manipulated fiber optically, and thus the excitation source can be positioned remotely from the sampling region. A particular fiber optic probe is described below; however, one skilled in the art will appreciate that the Raman spectrometer system is not limited to any particular means of radiation manipulation.

The scattered radiation is collected and dispersed by any convenient means known in the art, such as a fiber optic probe as described below. The collected scattered radiation is filtered to remove Raleigh scattering and then frequency (wavelength) dispersed using a suitable dispersive element, such as a blazed grating or a holographic grating, or interferometrically (e.g., using Fourier transforms). The grating can be fixed or scanning, depending upon the type of detector used. The monochromator 14 can be any such dispersive element, along with associated filters and beam manipulation optics.

The dispersed Raman scattering is imaged onto a detector 16. The choice of detector is easily made by one skilled in the art, taking into account various factors such as resolution, sensitivity to the appropriate frequency range, response time, etc. Typical detectors include array detectors generally used with fixed-dispersive monochromators, such as diode arrays or charge coupled devices (CCDs), or single element detectors generally used with scanning-dispersive monochromators or FT-based spectrometers, such as lead sulfide detectors and indium-gallium-arsenide detectors. In the case of array detectors, the detector is calibrated such that the frequency (wavelength) corresponding to each detector element is known. The detector response is delivered to the processor 30 that generates a set of frequency shift, intensity (x,y) data points which constitute the Raman spectrum.

The scattered radiation related to the polymerization material may be collected by a probe 24 in a variety of locations within the polymerization system 50. Exemplary locations depicted in FIG. 1 are in the reactor 62, in a product stream discharge line 64 downstream of reactor 62, in a separator system 68, in a recycle line 70, and/or in sample port 74 downstream of the reactor 62. It is understood that these probe locations are merely exemplary and that one or more probes 24 may be located in a variety of other locations within the high pressure polymerization system. The probe 24 delivers the excitation radiation from the light source 12 to the polymerization material, collects the scattered radiation, and delivers the scattered radiation to the monochromator 14 through the transmittance system 20.

With reference to FIG. 1, as discussed above, the polymerization system 50 may be monitored and controlled by the Raman spectrometer system 10. The exemplary polymerization system 50 comprises a primary compressor 54, a secondary compressor 58, a reactor 62, a sample port 74, and a separator system 68. In this embodiment a monomer feed stream comprising at least one monomer within the stream, such as but not limited to ethylene, is fed to the inlet of the primary compressor 54 via a feed line 52. The gas exiting the primary compressor 54 is discharged to a pressurized feed line 56 for delivery to the secondary compressor 58 for further pressurization. The further pressurized gas exiting the secondary compressor 58 passes to the reactor 62 through a reactor feed line 60.

Modifiers or monomers may be introduced into the pressurized feed line 56 from a side stream (not shown) as well as recycle gas via a recycle line 70 from the separator system 68. Further, the primary and secondary compressors of FIG. 1 can each be single stage compressor, multi-stage compressor, or at least two compressors in series or in parallel. The side streams may use separate compressors or lines from the primary or secondary compressors.

The reactor 62 may be comprised of a single shell pressure vessel capable of containing the high-pressure gas, or super-critical fluid such as in high pressure polyethylene production, within and forming a space for the polymerization reaction of the monomer. Preferably one or more catalysts or initiators are delivered to the reactor 62 and combined with the monomer for polymerization of the monomer within the reactor 62.

While the monomer can be any molecule or molecules capable of additional polymerization by either a free-radical mechanism or coordination catalytic mechanism, a particularly prevalent monomer used in high pressure polymerizations is ethylene. Other monomers which incorporate less easily and may have transfer-activity and a molecular weight limiting effect (and indeed can, for some purposes, be regarded as incorporating transfer agents) include: vinyl acetate, ethyl acrylate, methyl acrylate, butyl acrylate, and the like. Most commonly ethylene is used at a mole concentration of at least 90%, or 96%, or 98%, the percentages being based on the total weight of all monomer and transfer agents present.

While Ziegler-Natta catalysts can be used such as $TiCl_3$ based catalysts with an aluminum alkyl activator, or metallocene catalysts with an alumoxane or non-coordinating anion activator, or using a free-radical initiator, generally initiators can be selected from the list given in Ehrlich, P., et al., Fundamentals of the Free-Radical Polymerization of Ethylene, Advances in Polymer Science, Vol. 7, pp. 386-448, (1970).

Chain transfer agents, as described in U.S. Pat. No. 6,673,878 to Donck, may also be present in the reaction mixture.

Within the reactor 62 the process of converting the monomer into a polymer occurs by processes well known in the art. For example, in one known process, monomers are stripped of at least one of their associated hydrogen atoms that in turn allows monomeric bonding thereby forming polymeric chains comprised of these monomers. A step-by-step analysis of this process reveals certain intermediate polymeric compounds that can exist during the process of polymerization.

In another embodiment the reactor 62 may be a tubular reactor; one such embodiment comprises a convoluted tubular member wherein the length to diameter ratio is in excess of 1,000. As is known, tubular reactors typically comprise a reaction zone followed by a cooling zone. The polymerization reaction typically occurs within the reaction zone, this reaction is promoted by adding an above-mentioned initiator to the tubular reactor in the region of the reaction zone. Due to the exothermic reaction, the maximum temperature within tubular reactors generally occurs within the reaction zone. These high temperatures in turn require that the reactant material be cooled in the subsequent cooling zone. Cooling is provided to the exterior of the tubular reactor often in the form of a cooling water jacket. The design of each particular tubular reactor depends on its application and thus each tubular reactor can comprise more than one sequence of reaction zone followed by a cooling zone. It is well within the capabilities of those skilled in the art to establish an appropriate number and sequence of reaction and cooling zones for a tubular reactor.

The reaction process within the reactor 62 produces a reaction mixture comprising a polymeric product stream, a monomer rich phase, and some small portion of intermediate compounds that have been only partially polymerized. The primary constituents of the reaction mixture, i.e., the polymeric product stream and the monomer rich phase, are separated within the separator system 68. Here the monomer rich phase, also known as recycle gas, is fed through the recycle line 70 upstream of the secondary compressor 58. The polymeric product is discharged from the separator system 68 through a product stream line 72 for extrusion and/or other finishing process steps. An exemplary separator system is disclosed in U.S. Pat. No. 6,673,878 to Donck. The polymer product stream 72 removed from the separator system 68 may be vented to produce an offgas stream (not shown). In certain embodiments, a probe may be provided in the offgas stream to provide a compositional analysis of this stream.

Compositional values and a variety of characterization values for the polymerization material may be determined using the methods and systems described herein Exemplary values that may be determined for the polymeric materials contained in the polymerization material include melt index, density, viscosity, molecular weight, molecular weight distribution, additive concentrations, weight ratios of different polymers making up the polymerization material, die swell, melt flow rate, monomer content, comonomer content, modifier content, catalyst concentration, and combinations thereof. In certain embodiments, the values determined for the polymerization material determined are melt index, density, viscosity, melt flow rate, monomer content, comonomer content, and combinations thereof. In other embodiments, the determined values for the polymerization material are melt index, density, viscosity, monomer content, and combinations thereof. In still other embodiments, the determined values for the polymerization material are melt index and density, and combinations thereof.

For example, the methods and systems described herein may be used to determine the relative amount of individual monomers such as ethylene and vinyl acetate in the polymeric product contained in the polymerization material. In certain embodiments, the melt index, density, and combinations thereof of the polymer product material in the polymerization mixture may be determined by the methods and systems described herein. Also, the composition of the individual components of the reaction mixture may be determined. These characteristics can also indicate the integrity and/or quality of the final formed product.

Monitoring and evaluation of these characteristics can be accomplished on-line and real time with Raman spectroscopy during the polymerization process. The Raman monitoring can occur within the reactor 62 as well as downstream of the reactor 62, before and after the separator system 68.

Exemplary monitoring options are illustrated in FIG. 1 where Raman probes 24 are depicted as being located within the reactor 62, in the reactor polymer product stream discharge line 64, in the separator system 68, in the recycle line 70, and in a sample port 74 in the polymer product stream line 72 exiting separator system 68. The sample port 74 may simply be an aperture formed within the product stream line 72 or can be a dedicated piece of piping formed specifically to receive or house a Raman probe 24.

In embodiments, in which a probe is located in a sample stream, the sampling apparatus may be designed to continuously extract a slip stream of the desired polymerization material from the high pressure process and direct the stream to a probe and then return the extracted portion of the polymerization material to the high pressure process. Generally, it is desirable to conduct the analysis on a large amount of product therefore it is desirable to maintain the extracted portion of the polymerization material as a continuously flowing slip stream out of and back into the high pressure process. A gear pump may be implemented to ensure that the slip steam flows continuously past the probe. In certain embodiments, at least one gear pump may be used to maintain the slip stream at a velocity of about 0.1 m/s to about 1 m/s to ensure that the polymerization material provides sufficient friction to maintain the probe tip in a clean condition. In other embodiments, at least one gear pump may be used to maintain the slip stream at a velocity of about 0.5 m/s to about 1 m/s to ensure that the polymerization material provides sufficient friction to maintain the probe tip in a clean condition. In additional embodiments, at least one gear pump may be used to maintain the slip stream at a velocity of about 0.8 m/s to about 1 m/s to ensure that the polymerization material provides sufficient friction to maintain the probe tip in a clean condition.

In certain embodiments, the sampling system may be selectively isolated from the high pressure polymerization process through the use of one or more valves that may be selectively opened and closed as desired for sampling, discontinuing the sampling, or maintenance of the sampling system.

High pressure polymerization processes present unique temperature and pressure environments in which to conduct spectroscopic analysis of the polymerization material, as described herein. The nature of the polymerization material to be analyzed within the high pressure polymerization process may vary considerably. For example, within the reaction zone, the components of the polymerization material may exist in a supercritical fluid state. At lower pressures outside the reaction zone, the components of the polymerization material may exist in gaseous, liquid, and solid phases. Moreover, the polymerization material may exist in homogeneous and non-homogeneous forms. For example, under certain conditions, especially in lower pressure portions of the reaction system, the different phases of the polymerization material may form striations. The polymerization material may also experience laminar flow. In such flow patterns, solid components of the polymerization material may be present along the walls of the reaction system components while liquid phase components exist in the interior regions of the reaction system components. Additionally, depending on the location within the reaction system, the polymerization material may be clear or opaque.

The methods and systems described herein are capable of providing analysis of the polymerization material under these varied conditions. The focus point of the analysis probe may be optimized for the state of the polymerization material existing in the reaction system at the probe to ensure accurate analysis. In other words, the focus point of the analysis system may be varied to analyze the polymerization material under these varied conditions. Generally, if the polymerization material is in a non-homogeneous state, a more accurate analysis will be obtained if the focus point of the analysis probe is shorter. Correspondingly, if the polymerization material is in a homogeneous state, the focus point of the analysis probe should be longer than used for non-homogeneous materials to ensure more accurate analysis. This is found to be particularly true in homogeneous materials such as clear materials wherein a longer focus point is desirable for more accurate analysis.

In certain exemplary embodiments, an analysis probe having a focus point of about 50 μm to about 200 μm is used to analyze polymerization materials that are non-homogeneous. In other exemplary embodiments, an analysis probe having a focus point of about 50 μm to about 150 μm is used to analyze polymerization materials that are non-homogeneous. In additional exemplary embodiments, an analysis probe having a focus point of about 75 μm to about 100 μm is used to analyze polymerization materials that are non-homogeneous. In more particular exemplary embodiments, an analysis probe having a focus point of about 75 µm is used to analyze polymerization materials that are non-homogeneous.

In certain exemplary embodiments, an analysis probe having a focus point of about 400 µm to 700 µm is used to analyze homogeneous polymerization materials. In still other exemplary embodiments, an analysis probe having a focus point of about 500 µm to 650 µm is used to analyze homogeneous polymerization materials. In additional exemplary embodiments, an analysis probe having a focus point of about 575 µm to about 625 µm is used to analyze homogeneous polymerization materials. In more particular embodiments, an analysis probe having a focus point of about 600 µm is used to analyze homogeneous polymerization materials.

In embodiments in which analysis of polymerization material in the reaction zone or other areas of very high pressure within the reaction system are desired, the very high pressures within the reaction system must be taken into consideration. In certain embodiments, the analysis probe may emit and collect the excitation radiation into the polymerization material through one or more windows produced from materials such as sapphire to withstand the extreme pressures within the reaction zone. In other embodiments, the analysis probe delivering and collecting the excitation energy may be in the form of optical fibers routed through a small diameter tube in the reaction system. In certain embodiments, the small diameter tube may be an epoxy filled tube designed to withstand the extreme pressures of the reaction zone. In all such embodiments, it is important to note that safety precautions should be followed because of the high pressures of the reaction system. For example, any window and/or tube arrangements may be combined with metal backing plates designed to contain the high pressure polymerization material in the event of failure of the window and/or tube configurations. A reactor shut-down system triggered by failure of any of the analysis system components may also be used in certain embodiments. In other embodiments, failure of any of the analysis system components may trigger the closing of a valve or valves to close communication between the analysis system and the high pressure reaction system.

It is understood that the methods and systems described herein may be utilized by analyzing only the reaction mixture within the reactor 62, analyzing the polymer product stream within discharge line 64, analyzing the polymer product stream within the separator system 68, analyzing the recycle gas stream within the recycle line 70, analyzing the polymer product stream with sample port 74, or combinations thereof.

In one embodiment, the processor 30 compares the results of the Raman analysis with baseline data to ensure that the polymerization material of the polymerization system 50 is within acceptable operating specifications. Should the processor 30 detect an excursion from these specifications, the processor 30 may be programmed to provide control commands to the polymerization system 50. The control commands may be delivered to the polymerization system 50 via the control loop 32. The processor 30 may be programmed to recognize excursions from specified operating parameters and take necessary corrective action. It is also within the scope of one skilled in the art to develop a suitable control loop 32 for carrying control commands from the processor 30 to the polymerization system 50.

As discussed above, the processor 30 affects operation of the polymerization system 50 by directing control commands to the polymerization system 50 via the control loop 32. For example, the calculated polymerization material properties are compared to target properties, and at least one polymerization process parameter of the polymerization system 50 is adjusted based on the deviation between the calculated and target product properties. The at least one polymerization process parameter may include monomer concentration, comonomer concentration, catalyst concentration, cocatalyst concentration, reactor temperature, reactor pressure, the ratio of monomer feeds, the ratio of hydrogen to monomer, modifier concentration, recycle gas concentrations, and combinations thereof. For example, if the particular property determined is density, a reactor parameter can be adjusted to increase density, such as, for example, reducing the comonomer feed rate and/or increasing the monomer feed rate. In other embodiments, the at least one polymerization process parameter that may be adjusted is selected from monomer concentration, comonomer concentration, additive concentration, modifier concentration, reactor pressure, reactor temperature, and combinations thereof. In still other embodiments, the at least one polymerization process parameter that may be adjusted is selected from monomer concentration, reactor pressure, reactor temperature, and combinations thereof.

In other embodiments, the systems and processes described herein may be used to monitor certain conditions within the reaction system occurring on a transient basis. For example, in certain high pressure reaction systems, the temperature of the reaction zone may be raised to assist in the removal of foulant coatings on the reactor walls. During the removal of the foulant coating in this manner, the melt index of the polymeric material being produced changes while the foulant material removal is in progress. The systems and processes described herein may be used to monitor the melt index of the polymeric material to determine when removal of the foulant material is complete. After detecting completion of removal of the foulant material through melt index monitoring, the reactor may be returned to normal operating temperatures.

As noted above, the excitation radiation can be delivered to and collected from the polymerization material by any convenient means, such as using conventional optics or fiber optic cables. In certain embodiments, the transmittance system 20 includes a probe 24 connected to the Raman spectrometer system 10 via cables 22.

Figure 2:
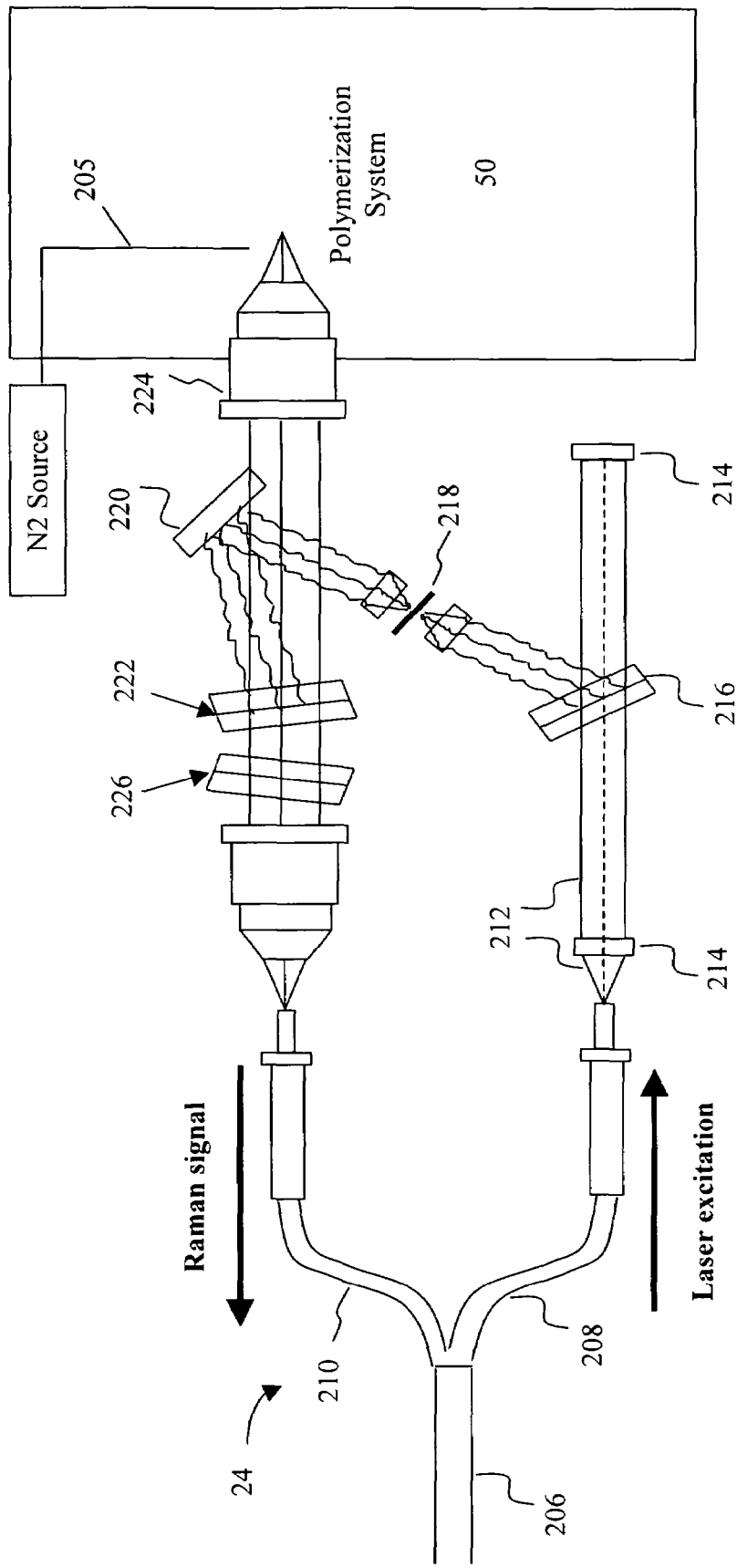
FIG. 2 depicts a fiber optic Raman probe in accordance with one embodiment of the methods and systems described herein.

FIG. 2 is a diagram of one embodiment of a fiber optic probe useful in the systems and processes described herein. The probe includes a fiber optic bundle 206 including one or more fiber optic cables 208 carrying the excitation radiation from the excitation source toward the polymerization material, and one or more fiber optic cables 210 carrying the collected scattered radiation from the polymerization material. Fiber optic cables 208 are in optical communication with the light source 12 (not shown in FIG. 2), and fiber optic cables 210 are in optical communication with the monochromator 14 (not shown in FIG. 2). The excitation and scattered radiation can be manipulated using well-known techniques. Thus, it should be appreciated that the particular optical setup shown in FIG. 2 is merely exemplary. Excitation radiation 212 is directed via optics 214 to a holographic grating 216 and spatial filter 218 to remove silica Raman due to the fiber optic cable, then directed via mirror 220 and beam combiner 222 to sampling optics (not shown) within probe head 224. Scattered radiation is collected via the sampling optics and directed through beam combiner 222, a notch filter 226 to remove the Raleigh scattered radiation, and into fiber optic cables 210.

Because static charge may buildup on the probe head 224, to dissipate static charge an optional grounding strap (not shown) can be used to ground the probe head 224.

In certain embodiments, an inert gas flow is provided via conduit 205. The inert gas, such as nitrogen gas, is directed via conduit 205 to provide a gas flow across the probe head 224 to reduce the incidence of probe fouling on the probe head 224.

Referring to FIG. 1, the processor 30 receives signals from the detector 16. The processor 30 can comprise a computer capable of storing and processing the Raman data. In one embodiment described above, the processor 30 controls the motion of the sampling probe. In yet another embodiment, the comparison of target to calculated values is relied on for adjusting the control of the polymerization system 50.

Figure 3:
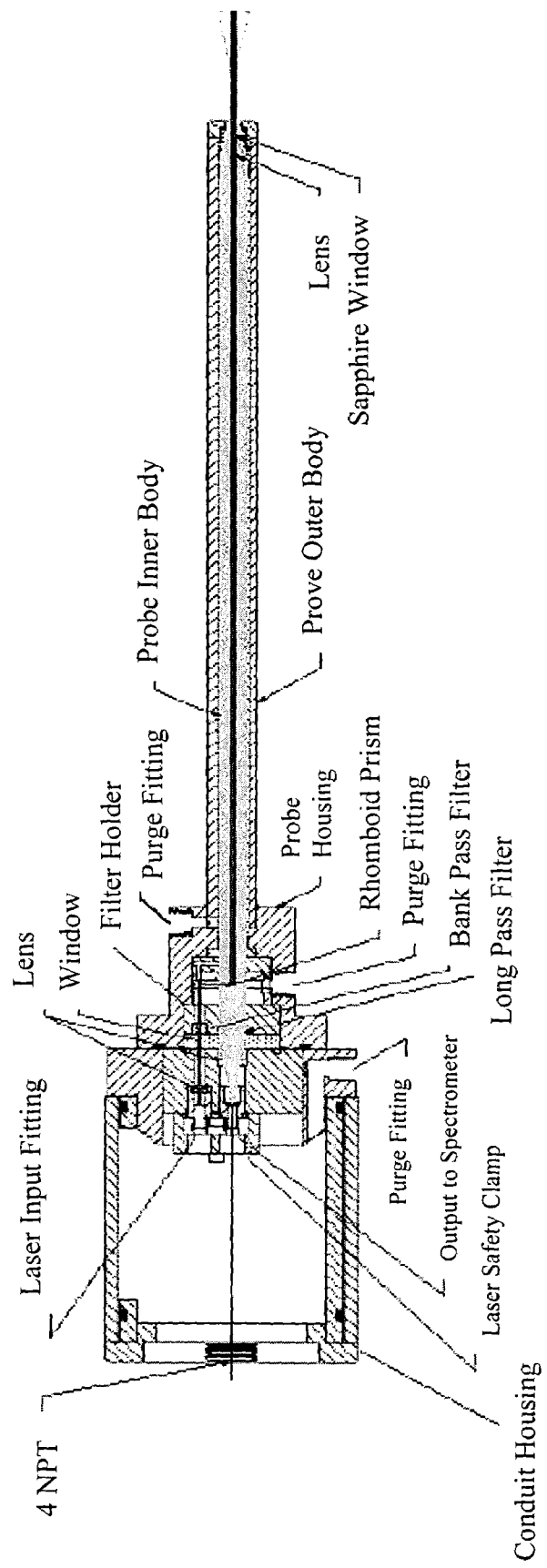
FIG. 3 depicts a Raman probe in accordance with one embodiment of the methods and systems described herein.

FIG. 3 provides a representation of another exemplary Raman probe suitable for use in accordance with the methods and systems described herein. The probe depicted in FIG. 3 is commercially available from Axiom Analytical Incorporated.

With respect to the various ranges set forth herein, any upper limit recited may, of course, be combined with any lower limit for selected sub-ranges.

All patents and publications, including priority documents and testing procedures, referred to herein are hereby incorporated by reference in their entireties.

Although the methods and systems described herein and their advantages have been described in detail, it should be understood that various changes, substitutions, and alterations could be made without departing from the spirit and scope of the inventions described herein as defined by the following claims.

What is claimed is:

1. A method of monitoring a high pressure reaction system comprising:
    (a) forming a polymerization material comprising: (i) a reaction mixture comprising monomer, solvent, and polymer product within a reaction zone maintained at a temperature of 120° C. to 355° C. and a pressure of 110 MPa to 350 MPa and (ii) polymer product downstream of the reaction zone;
    (b) irradiating at least a portion of the polymerization material;
    (c) measuring the energy shift experienced by the at least a portion of the polymerization material due to the step of irradiating; and
    (d) determining a characteristic of the at least a portion of the polymerization material based on the energy shift;
    wherein the at least one analysis probe has a focus point of about 50 μm to 200 μm for non-homogeneous polymerization materials and a focus point of about 400 to 700 μm for homogeneous polymerization materials.

2. The method of claim 1, wherein the characteristic of the at least a portion of the polymerization material is selected from the group consisting of melt index, density, viscosity, molecular weight, molecular weight distribution, additive concentration, weight ratios of different polymers making up the polymerization material, die swell, melt flow rate, monomer content, comonomer content, modifier content, catalyst concentration, and combinations thereof.

3. The method of claim 2, wherein the steps (b), (c), and (d) are conducted using at least one analysis probe and Raman spectroscopy and wherein the at least a portion of the polymerization material is at a pressure of about 0.5 MPa or higher.

4. The method of claim 3 comprising repeating steps (b), (c), and (d).

5. The method of claim 4, wherein the frequency of repeating steps (b), (c), and (d) ranges from about 1 minute to about 5 minutes.

6. The method of claim 5, wherein the reaction zone is maintained at a temperature of 120° C. to 355° C. and a pressure of 210 MPa to 310 MPa.

7. The method of claim 5, wherein the reaction zone is maintained at a temperature of 210° C. to 310° C. and a pressure of 110 MPa to 220 MPa.

8. The method of claim 6, wherein the step of irradiation comprises irradiating the polymerization material with a light source having a wavelength of from about 400 cm$^{-1}$ to about 1800 cm$^{-1}$.

9. The method of claim 8, wherein a first signal representative of the characteristic determined in step (c) is generated and transmitted to a processor.

10. The method of claim 9 comprising generating at least one control command with the processor and transmitting the control command from the processor to the polymerization process.

11. The method of claim 10, wherein the at least one control command provided to the high pressure polymerization process relates to control of a parameter selected from the group consisting of monomer concentration, comonomer concentration, catalyst concentration, cocatalyst concentration, reactor temperature, the ratio of monomer feeds, the ratio of hydrogen to monomer, and combinations thereof.

12. The method of claim 11, wherein the high pressure polymerization process is a continuous process and the at least a portion of the polymerization material is at a pressure of about 5 MPa or higher.

13. The method of claim 12, wherein the characteristic of the at least a portion of the polymerization material is selected from the group consisting of melt index, density, viscosity, melt flow rate, monomer content, comonomer content, and combinations thereof.

14. The method of claim 13, wherein the at least one control command provided to the polymerization process relates to control of a parameter selected from the group consisting of monomer concentration, catalyst concentration, reactor temperature, and combinations thereof.

15. The method of claim 1, wherein the at least a portion of the polymerization material is irradiated in at least two locations and the characteristic generated is generated for the polymerization material at the at least two locations.

16. The method of claim 10, wherein the at least a portion of the polymerization material is at least a portion of the reaction mixture and the at least a portion of the reaction mixture is irradiated within the reaction zone.

17. The method of claim 16, wherein the at least one control command provided to the high pressure polymerization process relates to control of a parameter selected from the group consisting of monomer concentration, comonomer concentration, catalyst concentration, cocatalyst concentration, reactor temperature, the ratio of monomer feeds, the ratio of hydrogen to monomer, and combinations thereof.

18. The method of claim 17, wherein the high pressure polymerization process is a continuous process.

19. The method of claim 18, wherein the characteristic of the at least a portion of the polymerization material is selected from the group consisting of melt index, density, viscosity, melt flow rate, monomer content, comonomer content, and combinations thereof.

20. The method of claim 19, wherein the at least one control command provided to the polymerization process relates to control of a parameter selected from the group consisting of monomer concentration, catalyst concentration, reactor temperature, and combinations thereof.

21. The method of claim 20, wherein the characteristic of the at least a portion of the polymerization material is selected from the group consisting of melt index, density, and combinations thereof.

22. The method of claim 20, wherein the at least a portion of the polymerization material is irradiated in at least two locations and the characteristic generated is generated for the polymerization material at the at least two locations.

23. The method of claim 10, wherein the at least a portion of the polymerization material is at least a portion of the polymer product downstream of the reaction zone and the analysis probe has a focus point of about 50 µm to about 150 µm.

24. The method of claim 23, wherein the at least one control command provided to the high pressure polymerization process relates to control of a parameter selected from the group consisting of monomer concentration, comonomer concentration, catalyst concentration, cocatalyst concentration, reactor temperature, the ratio of monomer feeds, the ratio of hydrogen to monomer, and combinations thereof.

25. The method of claim 24, wherein the high pressure polymerization process is a continuous process.

26. The method of claim 25, wherein the characteristic of the at least a portion of the polymerization material is selected from the group consisting of melt index, density, viscosity, melt flow rate, monomer content, comonomer content, and combinations thereof.

27. The method of claim 26, wherein the at least one control command provided to the polymerization process relates to control of a parameter selected from the group consisting of monomer concentration, catalyst concentration, reactor temperature, and combinations thereof.

28. The method of claim 27, wherein the characteristic of the at least a portion of the polymerization material is selected from the group consisting of melt index, density, and combinations thereof.

29. The method of claim 28, wherein the at least a portion of the polymerization material is irradiated in at least two locations and the characteristic generated is generated for the polymerization material at the at least two locations.

* * * * *